United States Patent [19]

Swan et al.

[11] Patent Number: 5,135,474
[45] Date of Patent: Aug. 4, 1992

[54] HEPATIC BYPASS CATHETER

[75] Inventors: Kenneth G. Swan, South Orange, N.J.; Charles J. Heyler, III, Carpinteria, Calif.

[73] Assignee: University of Medicine and Dentistry of New Jersey, Newark, N.J.

[21] Appl. No.: 562,314

[22] Filed: Aug. 3, 1990

[51] Int. Cl.$^5$ .............................................. A61M 5/00
[52] U.S. Cl. ...................................... 604/8; 604/101; 606/194
[58] Field of Search .................... 604/8, 96–104; 606/191–192, 194; 623/1

[56] References Cited

U.S. PATENT DOCUMENTS

| | | | |
|---|---|---|---|
| 2,927,584 | 3/1960 | Wallace | 604/96 |
| 3,884,242 | 5/1975 | Bazell et al. | 604/96 |
| 4,143,109 | 3/1979 | Stockum | 264/112 |
| 4,192,302 | 3/1980 | Boddie | 604/8 |
| 4,571,240 | 2/1986 | Samson et al. | 604/96 |
| 4,581,017 | 4/1986 | Sahota | 604/101 |
| 4,676,778 | 6/1987 | Nelson, Jr. | 604/101 |
| 4,705,502 | 11/1987 | Patel | 604/101 |
| 4,712,551 | 12/1987 | Rayhanabad | 604/96 |
| 4,889,744 | 12/1989 | Quaid | 623/8 |
| 4,950,226 | 8/1990 | Barron | 604/8 |

*Primary Examiner*—C. Fred Rosenbaum
*Assistant Examiner*—Chalin Smith
*Attorney, Agent, or Firm*—Michael G. Petit

[57] ABSTRACT

A hepatic bypass catheter comprising a triple lumen tube having a proximal end and a distal ends. Two balloon-like expandable segments are spaced about seven centimeters apart and located at the distal end of the tube two inflation couplers are connected to the two expander lumens at the proximal end thereby providing independent control over each expander. Several nine millimeter holes in the wall of the third, larger lumen are located on the proximal side of the second balloon. In practice, the distal end of the catheter is introduced into a femoral vein and the catheter advanced until the expanders are placed on each side of the hepatic venous junction with the inferior vena cava. Upon inflation of the expanders, and in conjunction with occlusion of the common hepatic artery and the portal vein, the liver is isolated from the circulatory system. Blood returning to the heart through the inferior vena cava bypasses this junction by entering the large lumen through the side holes traveling through the center of the balloons and continuing to the right atrium. The outer surface of the expander balloons are textured to reduce slippage while the inner surface of the balloons are coated with a non-blocking layer to facilitate inflation, even after long periods of storage.

2 Claims, 3 Drawing Sheets

HEPATIC BYPASS CATHETER

BACKGROUND OF THE INVENTION

1. Field of the Invention

This invention relates generally to surgical apparatus and more specifically to an improved catheter for use in performing liver surgery.

2. Definitions

The following terms, as used herein, shall have the following meanings:

"distal" refers to the end of a hepatic bypass catheter that is inserted into a patient.

"proximal" means the end of the hepatic bypass catheter that remains outside the patient.

"caudal" means that portion of the inferior vena cava below the junction of the hepatic veins and vena cava.

"cephalad" means that portion of the inferior vena cava above the junction of the hepatic veins and vena cava.

3. Discussion of the Prior Art

In the case of traumatic injury resulting in liver hemorrhage, chances of survival are slim due to current lack of ability to achieve zero blood pressure in the liver; a prerequisite to the surgical repair at the site of bleeding. In two recent studies of hepatic injury, (C. E. Lucus et al. "Prospective Evaluation of Hemostatic Techniques for Liver Injuries, " *J. Trauma* 1976;16:442-451 and D. V. Feliciano et al., "Management of 1000 Consecutive Cases of Hepatic Trauma (1979-1984) *Ann Surg* 1986; 204:439-445) only about ten percent of the patients required a major procedure for control of hemorrhage. In each study, blunt trauma was the most lethal, knife wounds least lethal, and gunshot wounds intermediate. In the last category, shotgun wounds were the most severe and approached blunt trauma in terms of morbidity and mortality. Most of those who succumb to their liver injuries, do so in the operating room. Three out of four hepatic injuries, regardless of cause, can be managed with simple measures such as laparotomy alone or in combination with suture or drainage.

Fabian and Stone (T. C. Fabian and H. H. Stone "Arrest of Severe Liver Hemorrhage by an Omental Pack." *South Med J* 1980; 73:1487-1490) reported a series of 113 cases of "massive liver injury". secondary to blunt trauma and treated with omental packing with a surprisingly low mortality of only eight percent. Feliciano et al. (D. V. Feliciano et al. "Intrabdominal Packing for Control of Hepatic Hemorrhage: A Reappraisal " *J. Trauma* 1981; 21:285-290) reported a small series of ten patients with extensive liver injury and hemorrhage unresponsive to standard techniques for control that were treated by intra-abdominal packing about the liver. The packs were removed either by re-operation or through drain sites and only one patient died.

To establish zero blood pressure in the liver to facilitate clotting and control hemorrhage, it is desirable to occlude the hepatic artery, the portal vein and the hepatic veins. Unfortunately, the retro hepatic inferior vena cava and hepatic veins are difficult to adequately expose for vascular control. Atrial-caval shunting is a useful technique along with the Pringle maneuver (temporary occlusion of the porta hepatis or portal vein, proper hepatic artery and common bile duct with a vascular clamp, Penrose drain, or thumb and forefinger). The latter procedure accomplishes hepatic inflow occlusion.

Atrial-caval shunting along with inflow occlusion has been used by Kudsk et al (K. A. Kudsk et al. "Atrial-Caval Shunting (ACS) After Trauma " *J. Trauma* 1984; 25:833-837) to treat eighteen patients with massive hemorrhage from the inferior vena cava, the hepatic veins or the liver with an operative mortality of 72%.

A number of devices for atrial-caval shunting have been described. They can be inserted by way of the right atrium or the right common femoral vein. The right atrial technique requires a right thoracotomy, or an extension of the mid-line laparotomy to a median sternotomy to expose the heart and isolate the supradiaphragmatic inferior vena cava with an umbilical tape. A large purse string suture is placed in the right atrium. An atriotomy is made and a large bore chest tube fenestrated proximally, inserted and clamped. The right atrial purse string suture is tied after the tube has been passed successfully beyond the hepatic and renal veins as determined by palpation from chest and abdominal exposures. The inferior vena cava is then encircled above the renal veins with an umbilical tape and the vena cava ligated about the tube above and below the injured segment. This technique isolates the suprarenal infradiaphragmatic inferior vena cava and arrests hemorrhage from the hepatic veins or vena cava without interfering with cardiac return. Because this technique requires manipulation of the heart, arrhythmia potentiated by acidosis and hypothermia may result.

Testas et al (American Journal of Surgery 133 pp. 692-696, Jun., 1977) describe a hepatic bypass catheter useful for vascular exclusion of the liver. Testas et al used a silastic triple lumen catheter containing two separately inflatable balloons near on end. The catheter was introduced into 35 dogs by means of the femoral vein. The correct positioning was controlled by a large medical incision, then vascular exclusion of the liver was performed by successfully inflating the caudal (proximal) balloon, clamping the hepatic pedical and finally inflating the upper (cephalad) balloon. While the investigators observed coagulation in the catheter, pre-treatment of the catheter with heparin prevented such coagulation in further studies.

SUMMARY OF THE INVENTION

The present invention is an hepatic bypass catheter assembly incorporating means whereby the lumen of the inferior vena cava may be occluded both cephalad and caudal (above and below) the junction of the hepatic veins and vena cava and still permit shunting of blood flow around the occlusion. When the flow of blood through the hepatic artery and fortel vein is blocked, the catheter is useful for reducing blood pressure in the liver to facilitate clotting of hemorrhaging vessels during and after surgery. For example, when performing liver surgery, the catheter is advanced through the femoral vein with the cephalad end entering the inferior vena cava. The caudal end is advanced long the inferior vena cava until the first balloon passes the hepatic vein as indicated by a radiopaque marker in the distal end of the catheter distal the balloon. Once the distal balloon on the top of the catheter is past the hepatic veins, the remaining balloon will be on the caudal side of the hepatic veins. The hepatic artery is first compressed either manually or with a tourniquet or clamp, thereby occluding it, and both balloons are then inflated, caudal first, then cephalad. The inflated balloons block the passage of caval blood to the hepatic vein. Fenestrations in the wall of the tubing permit blood to enter the lumen of the tubing and pass through the end of the catheter above the diaphragm.

The catheter itself comprises an elongated tubular member having an expander (balloon) near its distal end. A second expandable balloon is disposed approximately five to ten centimeters behind, or proximal to, the distal balloon. Radiopaque markers on the wall of the tubular member provide a visual index for determining the position of the balloons within the vena cava with respect to the hepatic veins. The wall of the tubular member is provided with ports opening into the interior of each balloon which ports are connected in fluid communication with an exterior fill member. Thus, by injecting fluid into the lumen of the tubular member at its proximal end, each expander can be separately inflated. Disposed proximal to the proximal balloon expander, are a series of holes in the wall of the tube opening to the central lumen. Once the two balloons are expanded, the inferior vena cava is occluded on either side of the hepatic veins, blood enters the lumen of the tube through the holes, passes through the tube and out the distal end thereby bypassing the hepatic vein.

It is accordingly a principal object of the present invention to provide a new and improved catheter assembly for performing hepatic venous bypass during liver surgery.

Yet another object of the invention is to provide a catheter assembly which can be readily inserted through a femoral vein, or elsewhere within the vascular system, and advanced to a predetermined point for the purpose of occluding and bypassing a segment of the vascular system.

Still another object of the invention is to provide a hepatic bypass catheter assembly of the above character in which two or more independently distendable expander members are disposed on the catheter near its distal end and which can be individually and independently inflated to occlude the flow of blood through a segment of the vascular system, without interrupting the flow of blood through the vessel itself.

Yet a further object of this invention is to provide radiopaque means for ascertaining the position of a hepatic bypass catheter within the inferior vena cava prior to inflation of the expander members.

Still another object of this invention is to provide a hepatic bypass catheter with textured expandable balloon portions which prevent slippage of the catheter following placement and inflation of the balloons.

Yet a further object of this invention is to provide a hepatic bypass catheter with an inflatable balloon portion wherein the balloons have a non-blocking inner surface to facilitate deployment.

Additional objects and features of the invention will appear from the following description in which the preferred embodiment is set forth in detail in conjunction with accompanying drawings in which, like numerals in the several views, refer to corresponding parts.

DESCRIPTION OF THE PREFERRED EMBODIMENT

Figure 1:
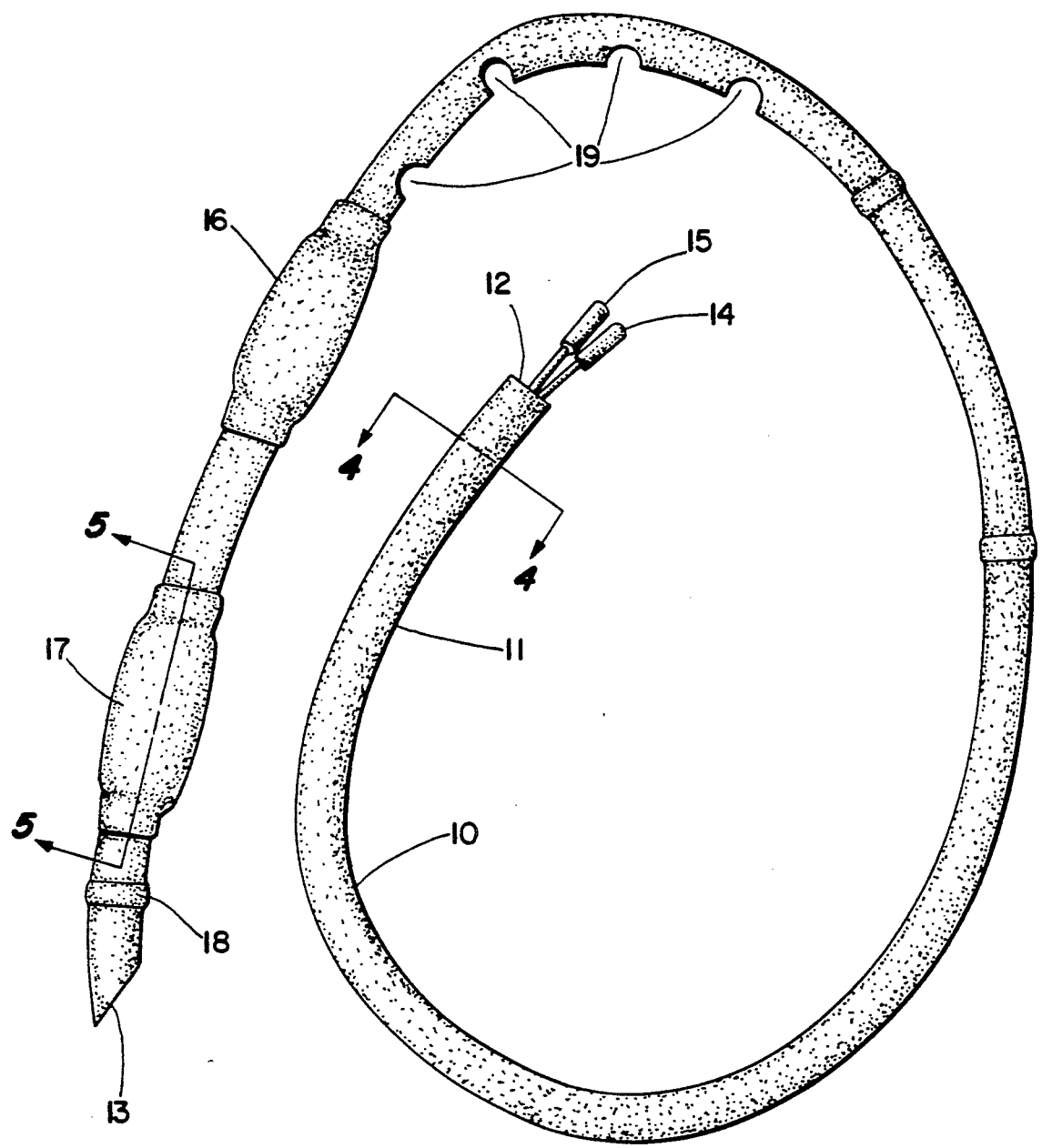
FIG. 1 is a side elevation view of the hepatic bypass catheter in accordance with the present invention.
Figure 4:
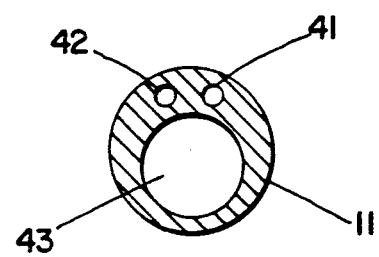
FIG. 4 is a cross sectional view of the catheter of FIG. 1 taken along 4—4.

Referring first to FIG. 1, there is indicated generally by numeral 10 an improved catheter in accordance with the preferred embodiment of the invention. While the catheter 10 will be shown and described as a catheter intended to be used during liver surgery, it is to be understood, following the teachings of the present invention, that it can be used in bypassing portions of the vascular system other than the hepatic veins and, accordingly, the invention is not to be limited to the hepatic vein bypass application only. The hepatic bypass catheter assembly 10 includes an elongated flexible silicone outer tubular member 11 which, for reasons which shall become apparent from the following description, is referred to as the expander mounting tube. The member (11) has a proximal end (12) and a distal end (13). The proximal end (12) of the catheter assembly joins to two luer-lock couplers (14 and 15) of conventional design, the coupler allowing a syringe or other tubular members to communicate with either of the two lumens (41 and 42) (FIG. 4) contained within the wall of outer tubular member 11. Depending upon the particular application, other suitable adapters may be employed to connect the couplers (14, 15) of the hepatic bypass catheter to appropriate fluid sources.

The expander mounting tube 11 may typically be a six French catheter but limitation to such a size is not to be inferred. Also, it may be found expedient to taper the distal end of the expander mounting tube 11 to facilitate its entry through an ostium and into the femoral vein.

Figure 5:
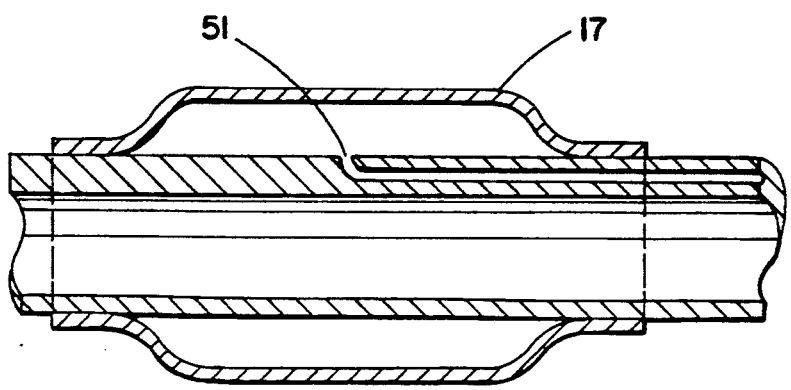
FIG. 5 is a cutaway view taken along 5—5 of FIG. 1 showing the portion of the hepatic catheter bearing the distal balloon.

Surrounding the distal portion of the expander mounting tube 11 is a proximal expander 16 which, in FIG. 1 is shown in its partially extended or inflated condition, and a distal expander 17 also shown in its expander inflated condition. The expanders 16 and 17 are preferably formed from a suitable synthetic elastomer such as biaxially oriented silicone. The expanders may be formed in an injection blow molding operation such that they are elastic in the radial direction but substantially inelastic in the axial direction. Preferably the expander members are suitably bonded to the outer surface of the expander mounting tube (11) so that the port formed through the side wall of the expander mounting tube (51) (FIG. 5) and communicating with its lumen is spanned by the expander member (17). Introduction of fluid through coupler (14) (will flow) through the lumen (41) of the expander mounting tube 11 and through the port (51) so as to inflate the distal expander member or balloon (17) to its maximal design diameter.

Formed proximally of the distal expander member is a second expander member, the proximal expander, similarly positioned on the surface of the expander mounting tube 11. Like the distal expander, the proximal expander member may be formed by bonding a relatively thin section of silicone tubing over the expander mounting tube (11) to span the proximal expander fill port (not shown). The proximal expander may be inflated by injection of fluid such as sterile saline into the expander by means of the proximal expander coupler (15) which is in fluid communication with the proximal expander fill port (not shown) by means of the proximal expander lumen (42).

A problem encountered with inflating silicone balloons is sticking. A smooth, untreated elastomer surface has the physical characteristic of blocking; that is, the characteristic of sticking to itself or other surfaces. Various lubricants and release agents have been dusted or otherwise applied to silicone articles to prevent blocking. The possible shedding of these lubricants would seriously contaminate the patient if a balloon burst during inflation. To prevent blocking, the inner surface of the balloons is preferably coated with a non-blocking layer of elastomer. A method for making such a non-blocking layer is described, for example, by Stockum in U.S. Pat. No. 4,143,109.

The outer surface of the balloon is in contact with the inner vascular wall. It is desirable to texture the outer surface of one or both balloons in such a way as to reduce the possibility of slippage or dislocation of the catheter after the balloon(s) are inflated. A method for texturing the outer surface of silicone articles such as balloons is described by Quaid in U.S. Pat. No. 4,889,744.

Figure 2:
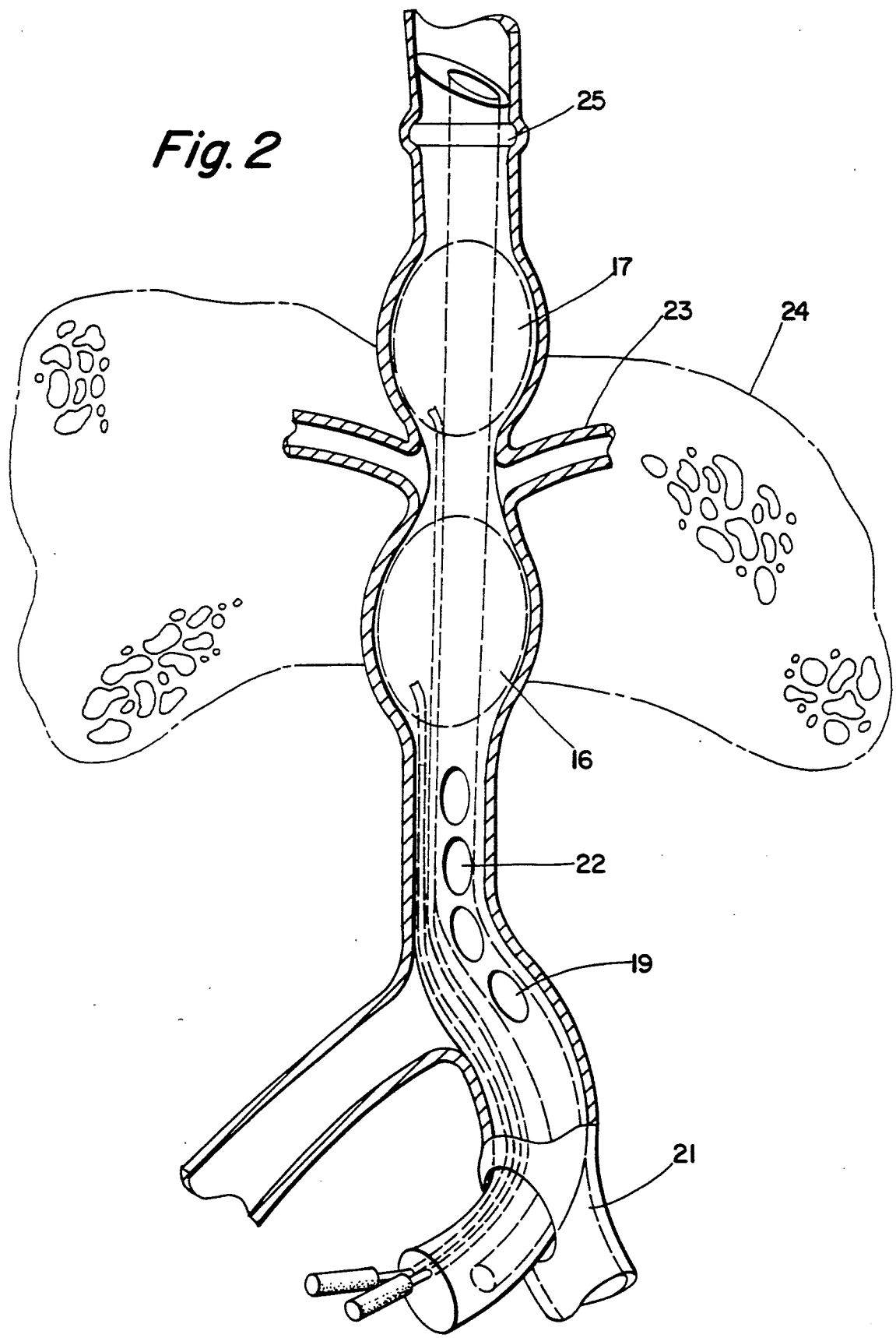
FIG. 2 is an enlarged, partially cutaway, side view of the distal end of the hepatic bypass catheter (FIG. 1) positioned within and occluding the vena cava proximally and distally with respect to the hepatic veins during hepatic bypass.
Figure 3:
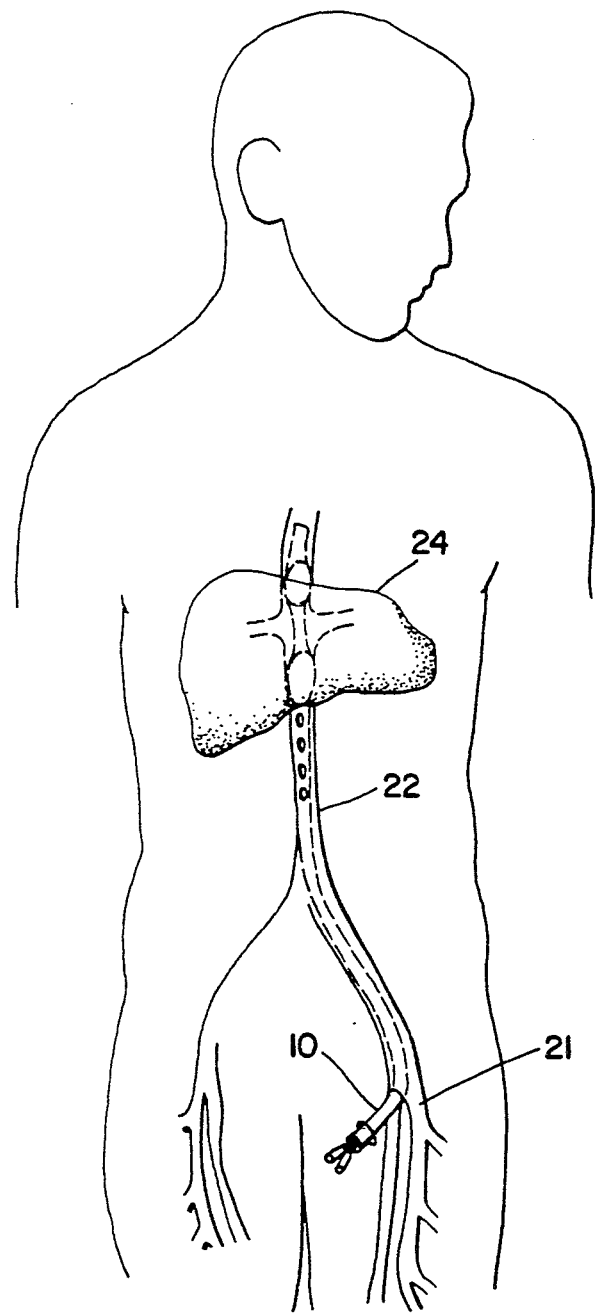
FIG. 3 is a schematic view of the catheter of the present invention entering a femoral vein and positioned within the inferior vena cava during hepatic bypass.

Performing a hepatic bypass can best be understood by turning now to FIG. 2. In practice, the distal end of the hepatic bypass catheter (10) is introduced into a femoral vein (21) and advanced into the inferior vena cava (22). The catheter is further advanced until the distal expansion member is past the juncture of the hepatic vein as verified by the position of the distal radiopaque marker (18).

In the preferred embodiment, the expander tube couplings 14 and 15 are of unequal length; the proximal coupler (15), which extends into the lumen which communicates with the proximal expander being longer than the coupler (14) which is in fluid communication with the distal expander (17). When the expansion members are positioned within the vena cava proximally and distally to the hepatic venous junction (23) the proximal and distal expansion members are inflated and the hepatic artery (not shown) is clamped thereby isolating the lumen from the circulatory system. Blood returning to the heart through the inferior vena cava bypasses the junction by entering the large lumen (43) of the bypass catheter through side holes (19). The blood then passes through the large lumen, past the proximal and distal expansion members and out the distal tip of the catheter (13) to the right atrium of the heart.

The hepatic bypass catheter described herein can also be used to infuse blood by inserting an intravenous tube directly into the proximal end of the catheter through the central lumen port (FIG. 1(12)). This insertion is not to be limited by the embodiments shown in the drawings and described in the specification, which are given by way of example and not of limitation, but only in accordance with the scope and spirit of the appended claims.

What I claim is:

1. A bypass catheter for preventing the flow of blood between a first blood vessel and a second blood vessel, said first blood vessel intersecting said second vessel to form a tee, said second blood vessel having a central channel passing therethrough into which said bypass catheter may be inserted, said bypass catheter comprising in combination:
   (a) an elongated tubular body having an outer wall with two longitudinally extending expander lumens embedded within said outer wall, a longitudinally extending greater lumen, and a proximal end and a distal end with two expander members affixed near said distal end, at least one of said expander members having a unitary textured silicone outer vessel-contacting surface comprising a plurality of pores or interstices in an otherwise smooth outer surface, said expander members being in fluid communication with said expander lumens of said tubular body;
   (b) a coupling means connected to the proximal ends of said expander lumens for injecting a fluid into said expander members; and
   (c) holes in the wall of said elongate tubular body providing fluid communication between said greater lumen and said central channel.

2. The bypass catheter of claim 1 wherein said first blood vessel is the hepatic vein and said second blood vessel is the inferior vena cava.

* * * * *